United States Patent [19]
Hauck

[11] Patent Number: 6,012,487
[45] Date of Patent: Jan. 11, 2000

[54] PRIME PURGE INJECTION VALVE OR MULTI-ROUTE SELECTIONS VALVE

[75] Inventor: Brian A Hauck, Santa Rosa, Calif.

[73] Assignee: Brian A. Hauck, Windsor, Calif.

[21] Appl. No.: 09/046,932

[22] Filed: Mar. 23, 1998

Related U.S. Application Data

[63] Continuation-in-part of application No. 08/814,445, Mar. 10, 1997, abandoned.

[51] Int. Cl.[7] .................................................. F16K 11/074
[52] U.S. Cl. ................................ 137/625.11; 137/625.46; 73/863.72
[58] Field of Search .......................... 137/625.11, 625.46, 137/625.47; 73/863.72, 863.73

[56] References Cited

U.S. PATENT DOCUMENTS

| | | | |
|---|---|---|---|
| 2,751,034 | 6/1956 | Ringo et al. | 137/625.11 X |
| 3,297,053 | 1/1967 | McKinney | 137/625.46 |
| 3,368,385 | 2/1968 | Harvey | 73/863.72 |
| 3,411,525 | 11/1968 | Auger | 137/625.46 X |
| 3,477,207 | 11/1969 | Auger | 137/625.46 X |
| 3,508,582 | 4/1970 | Aulisa | 137/625.11 |
| 3,747,630 | 7/1973 | Hurrell | 137/625.46 X |
| 3,868,970 | 3/1975 | Ayers et al. | 137/625.46 |
| 4,294,285 | 10/1981 | Joslyn | 137/625.11 |
| 4,367,645 | 1/1983 | Froment | 73/863.72 |
| 4,444,066 | 4/1984 | Ogle et al. | 73/863.72 |
| 4,552,178 | 11/1985 | Olsson | 137/625.46 |
| 4,614,204 | 9/1986 | Dolejs | 137/625.11 |
| 4,625,569 | 12/1986 | Toei et al. | 73/863.72 X |
| 4,690,179 | 9/1987 | Bleth et al. | 137/625.46 X |
| 4,705,627 | 11/1987 | Miwa et al. | 137/625.46 X |
| 4,926,702 | 5/1990 | Stephens et al. | 73/864.83 |
| 5,010,921 | 4/1991 | Nohl | 137/625.46 |
| 5,105,851 | 4/1992 | Fogelman | 137/625.11 |
| 5,390,552 | 2/1995 | Demachi et al. | 73/863.73 |
| 5,595,211 | 1/1997 | Adams | 137/625.46 X |
| 5,803,117 | 9/1998 | Olsen et al. | 137/625.15 |

Primary Examiner—John Rivell

[57] ABSTRACT

A valve is described for loading a sample at low pressure and injecting said sample into a high pressure stream, and for priming or purging of a high pressure pump. Also described is a multi-route selection valve which allows the selection of alternate flow routes through an analyzing instrument. Both valves have a rotor (11) that can pivot about an axis (13) and at the interface (12) the rotor creates a fluid tight seal against the stator (10). The stator has a common port and n peripheral ports where n is the maximum number of peripheral ports equaling an odd integer greater than or equal to 5. The rotor has a lateral face which is comprised of a distribution channel (7) and (n+1)/2−1 switching channels (8,9). The distribution channel (7) connects the common stator port (1) independently to each of the n peripheral ports (2–6). The switching channels (8,9) each span circumferentially through an arc circle of angle 360/n degrees (17). Switching channels (8) and (9) communicate flow between a plurality of adjacent peripheral stator ports as the rotor turns.

15 Claims, 13 Drawing Sheets

FIG. 4B
INJECT

FIG. 4C
PRIME/PURGE

FIG. 4A
LOAD

FIG. 13A
(PRIOR ART)
LOAD

FIG. 13B
(PRIOR ART)
INJECT

PRIME PURGE INJECTION VALVE OR MULTI-ROUTE SELECTIONS VALVE

This application is a C-I-P of application Ser. No. 08/814,445, filed Mar. 10, 1997, now abandoned.

BACKGROUND OF THE INVENTION

1. Field of the Invention

The present invention relates to High Performance Liquid Chromatography (HPLC) and the other analytical methods involving flowing liquid streams which are well known techniques for separating the constituent elements in a given sample. More specifically, the present invention relates to prime/purge, injection, and column selections valves used in HPLC systems.

2. Background Information

Figure 1:
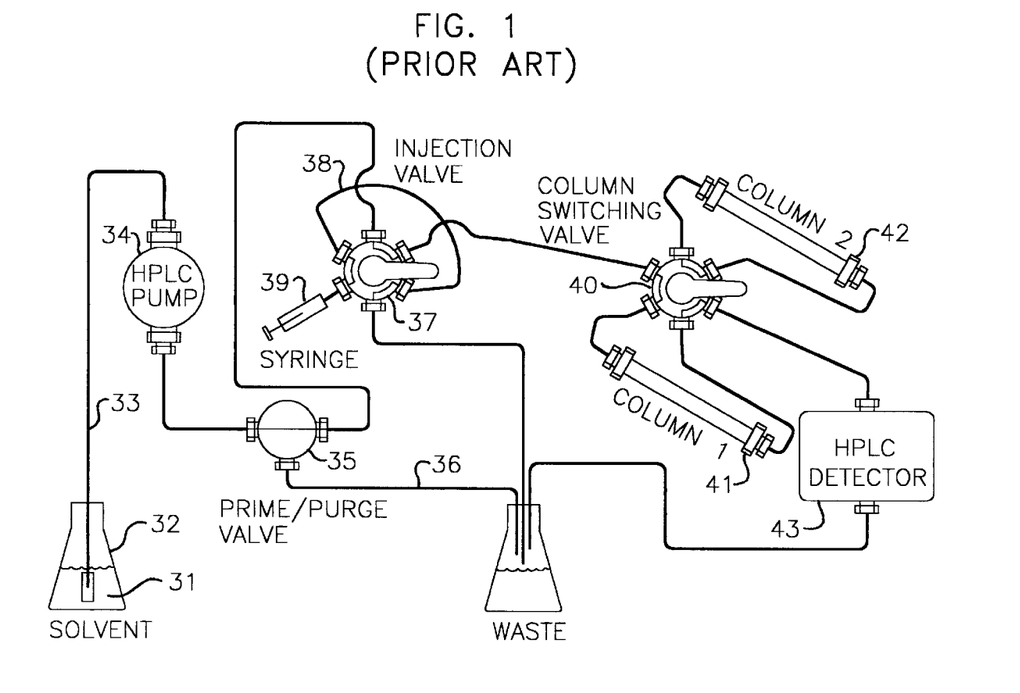
FIG. 1 is prior art for a block diagram of a High Performance Liquid Chromatographic system.

FIG. 1, a block diagram illustrates a typical environment in which the present invention will be utilized, with the elements of a prior art HPLC system shown. Liquid solvent 31 (often called the "mobile phase") is introduced from a solvent reservoir 32 and delivered via tubing 33 to a pump 34. This pump creates a vacuum which draws the solvent through the tubing and into the pump. The solvent will then exit the pump at a much higher pressure (typically in the range between 500 and 7000 psi) and then passes the solvent through a prime/purge valve 35.

As the name suggests, a prime/purge valve when opened permits priming of the pump during system startup by simply venting the pump outlet to atmospheric pressure via a waste outlet 36. An alternate method of priming the pump is by connecting a large syringe or other vacuum generating device to this waste outlet 36 and drawing the solvent from the reservoir through the pump 34. The other function of a prime purge valve is to permit rapid solvent change-out by allowing the purging of the pump and associated plumbing of any unwanted solvent.

After the prime/purge valve, a sample injection valve 37 permits loading a sample into a sample loop 38, using a syringe 39 or other metering device. When the valve is switched to the inject position, the sample contained within the sample loop is transferred at high pressure into a chromatographic column 41 or 42.

In some HPLC systems a column switching valve 40 is incorporated to permit the selection between two or more columns 41 and 42 and to permit various flow routes through these columns.

When the sample that was introduced via the injection valve is carried through a column (along with the mobile phase), the various components (solutes) in the sample migrate through the column at different rates due to the solute's affinity to the column packaging material. Because of the different rates of movement of the solutes, the sample components gradually separate as they move through a column. After exiting the column, the sample (as separated) is carried to a detector 43 which detects the presence or absence of various ions or molecules.

In these analytical methods, it is desired to minimize the holdup volume of the system and to eliminate any unswept volumes in the flow path. The minimized holdup volume is desired because it facilitates the rapid and complete replacement of one solvent for another and efficient gradient mixing. Unswept volumes are avoided, as an unswept volume can allow diffusion of sample into the unswept area or allow diffusion of carrier fluid (or a previous sample) out, thus diluting the sample and decreasing the resolution and sensitivity of the analytical method.

Figure 5A:
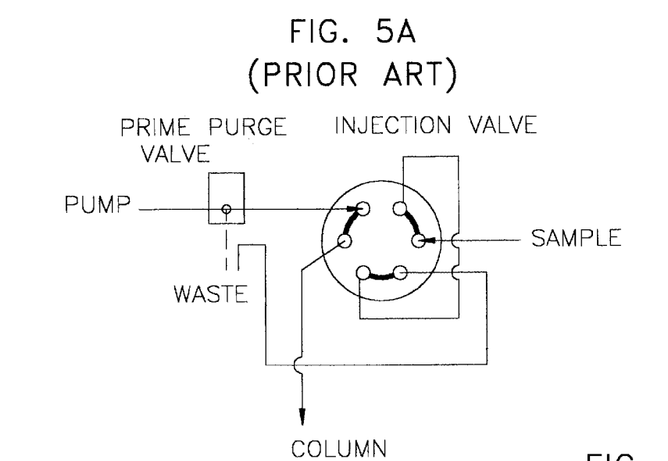
FIG. 5A is prior art of a simplified flow diagram for a prime/purge valve and an injection valve, with the injection valve shown in the load position, this view is similar to the preferred invention shown in FIG. 3A and FIG. 4A.
Figure 5B:
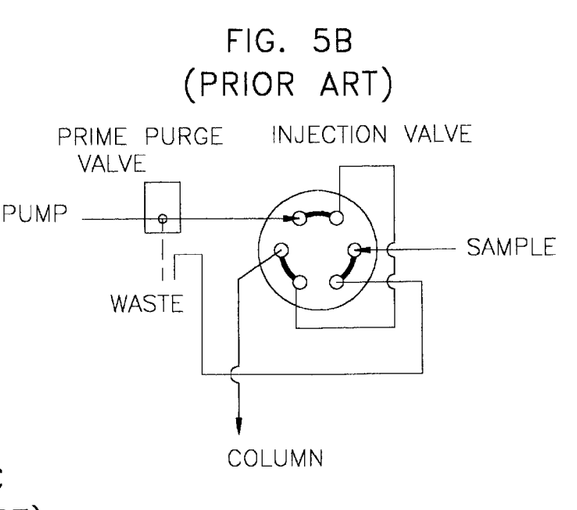
FIG. 5B is prior art of a simplified flow diagram for a prime/purge valve and an injection valve, with the injection valve shown in the inject position, this view is similar to the preferred invention shown in FIG. 3B and FIG. 4B.
Figure 5C:
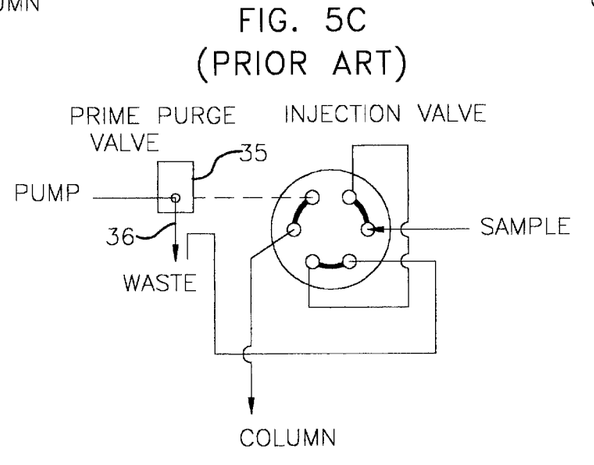
FIG. 5C is prior art of a simplified flow diagram for a prime/purge valve and an injection valve, with the prime/purge valve shown in the open position, this view is similar to the preferred invention shown in FIG. 3C and FIG. 4C.

FIG. 5A, is prior art which illustrates one type of sample injection valve with an associated prime/purge valve. The injection valve includes a disc shaped rotor with three circumferential channels on its front face. The rotor face extends perpendicular to its axis of rotation, which lies face wise adjacent to the face of a stator. The stator has six ports which lie on a port circle and extend axially to a rear face. An external sample loop of known volume can be connected to two of these ports. A sample can then be introduced to the sample loop through one of the stator ports thus filling the sample loop. When the rotor is turned 60° (FIG. 5B), solvent from a high pressure pump pumps the sample through the sample loop and corresponding stator passages into the chromatographic column. Model 7010 of Rheodyne L. P. (see Rheodyne Catalog #6 Page 6) is an example of such an injector. FIG. 5C illustrates the associated prime/purge valve in the open position. Flow from the pump, bypasses the injector valve and column entirely, and is directed to a waste container where the back pressure is essentially atmospheric. This prior art injector permits sample injection into a chromatographic system but requires an additional prime/purge valve to permit the priming or purging of a pump.

Figure 13A:
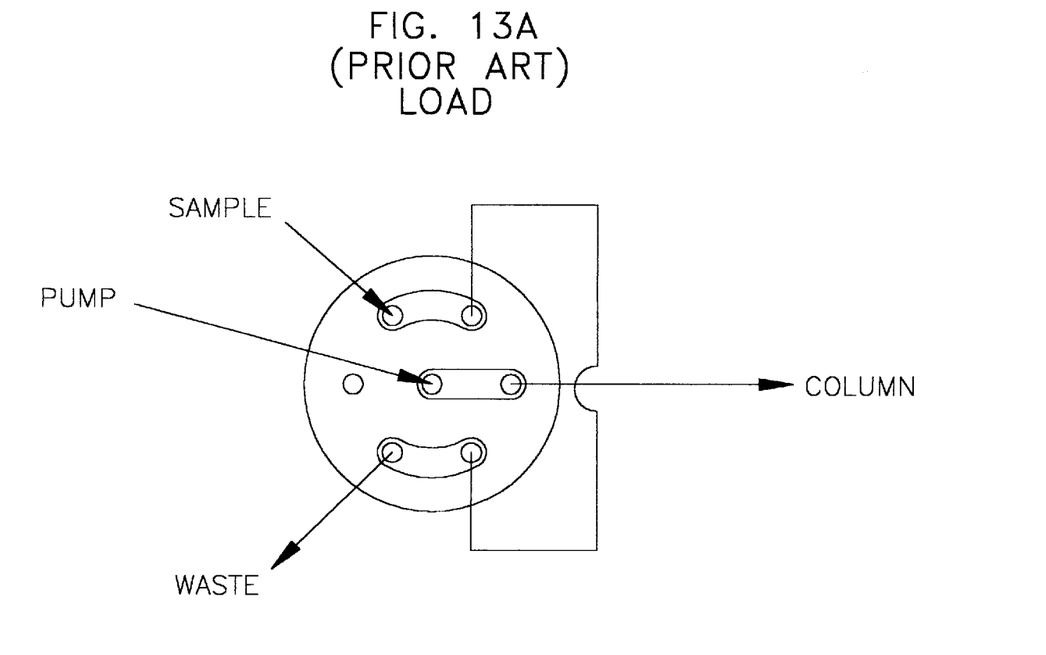
FIGS. 13A–13B are prior art for a possible prime/purge/injection valve in the LOAD and INJECT positions respectively.
Figure 13B:
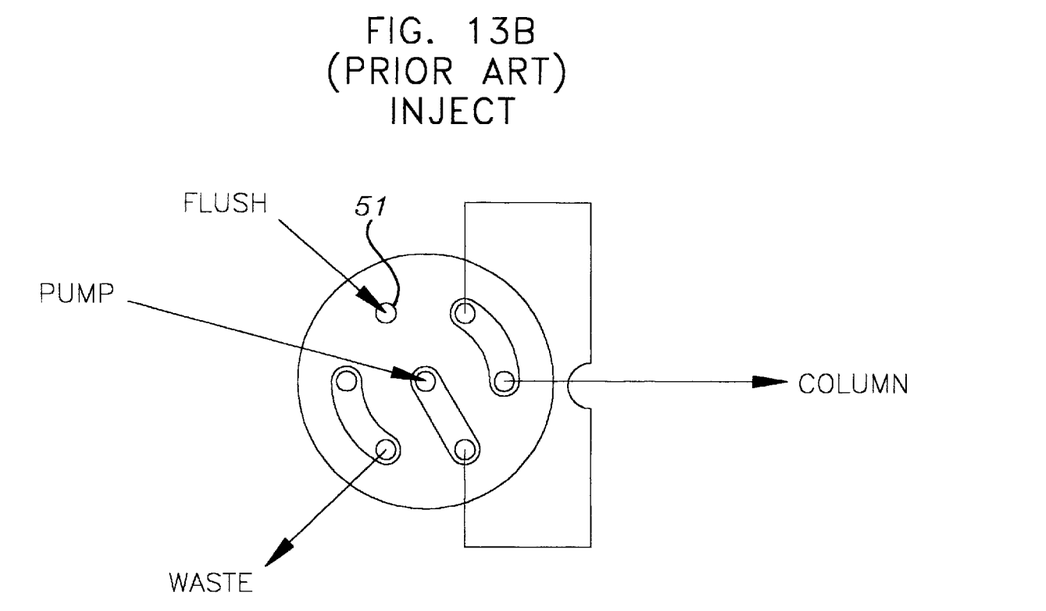

Fogelman describes a valve (U.S. Pat. No. 5,105,851) which could permit both sample injection and prime/purge capabilities but Fogelman's design does not permit flushing of the sample port when the valve is in the inject position. FIG. 13A and 13B show a Fogelman design in both the "LOAD" and "INJECT" positions respectively. FIG. 13B shows that when the valve is in the inject position, any sample remaining in port 51 can not be flushed since the port is dead ended against the rotor seal. This inability to flush the sample port 51 would be undesirable since any sample remaining in the port from a previous injection would cause contamination of the next sample to be loaded. There is a need for a single multi-position valve that permits both sample injection and prime/purge capabilities thus reducing the overall system holdup volume.

Figure 9A:
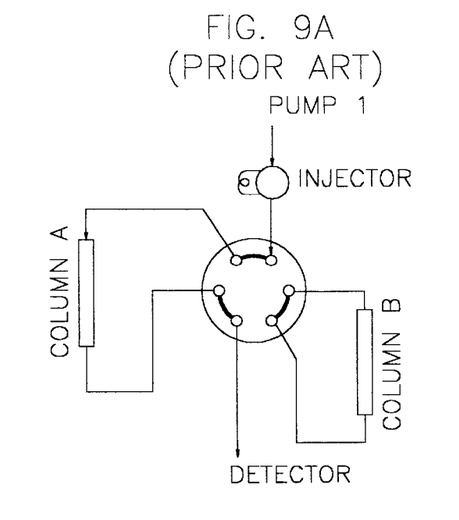
FIG. 9A is prior art of a simplified flow diagram for a column selection valve plumbed to allow the selection between two separate columns. The rotor is positioned to allow flow through column A while column B is off-line (the off-line column is sealed by connecting head to tail).
Figure 9B:
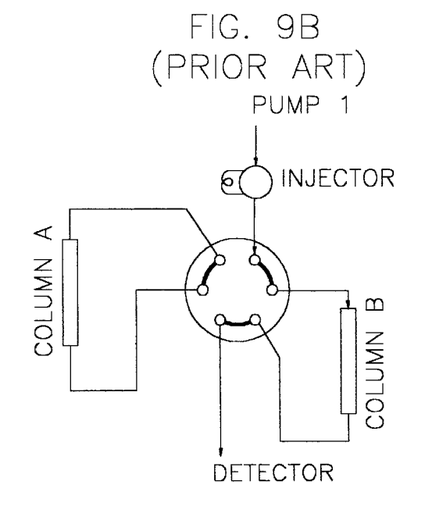
FIG. 9B is prior art which is similar to FIG. 9A but the rotor is positioned to allow flow through column B while column A is now off-line.

FIGS. 9A and 9B are prior art for one type of column selection valve which includes a disc shaped rotor with three circumferential channels on its front face that lies face wise against the stator rear face. Pivoting the rotor 60° enables these channels to connect to different columns depending on the position of the valve. FIG. 9A shows the column selection valve with flow passing through column A while column B is connected head to tail. When the rotor is pivoted 60° as shown in FIG. 9B, column A is now connected head to tail, and flow passes through column B. Model 7000 of Rheodyne L. P. (see Rheodyne Catalog #6 Page 17) is an example of this type of column selection valve. This valve has no unswept volume in any part of the flow path, but selection is limited to only two alternate paths.

Figure 8A:
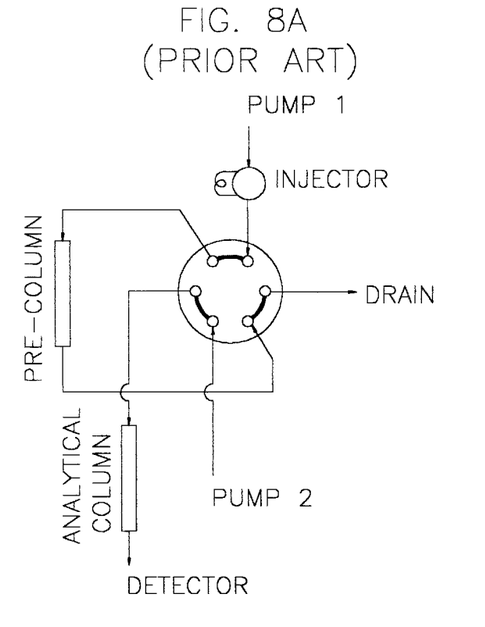
FIG. 8A is prior art of a simplified flow diagram for a column selection valve plumbed to allow sample enrichment. The rotor is positioned to allow sample from the injector to be concentrated on the pre-column while pump 2 delivers solvent directly to the analytical column.
Figure 8B:
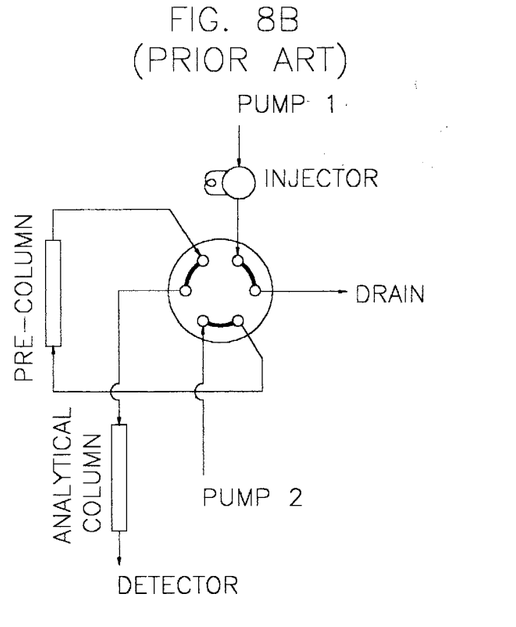
FIG. 8B is prior art which is similar to FIG. 8A but the rotor is positioned to allow the sample that was concentrated on the pre-column to be back flushed onto the analytical column using solvent from pump 2.

In some chromatographic analysis where large sample volumes are injected, it may be desirable to use a sample concentration scheme known as sample enrichment. FIGS. 8A and 8B are prior art for this concentration scheme which consists of injecting large volumes of sample into a pre-column, where trace components are concentrated. FIG. 8A shows an injector valve which can inject a large sample onto the head of the pre-column where the sample can be concentrated. Simultaneously, flow from a second pump delivers solvent through an analytical column. After valve switching (FIG. 8B), the enriched sample is back flushed off the pre-column and onto the analytical column by use of the second pump.

Fogelman's valve when plumbed as a column selector permits the selection between 2 or more columns and a bypass. The disadvantage of this design is that since there is always a single peripheral stator port that is dead-ended to the rotor seal in every position, this prevents the "off-line" columns from being connected head-to-tail, thus allowing the pressure in these columns to decay. Those knowledgeable in the field of chromatography would agree that in many instances, it is desirable to maintain pressure in the "off-line" column to facilitate the rapid re-equilibration of the column when it is brought back "on-line".

There exists a need for a multi-route selection valve that permits sample enrichment using a single pump and permits selection between two columns and a bypass.

SUMMARY OF THE INVENTION

The present invention provides either an improved injection valve with prime/purge capabilities or an improved column selection valve with bypass and sample enrichment capabilities. Both valves include a stator and a rotor element. The stator has a common port and n peripheral ports where n is the maximum number of peripheral ports equaling an odd integer greater than or equal to 5. The rotor is comprised of a distribution channel and (n+1)/2−1 switching channels. The distribution channel provides fluid communication between the common stator port and at least one of the peripheral stator ports. The switching channels preferably span an arc circle of 360/n°, and provide an uninterrupted flow path between pairs of adjacent peripheral stator ports. Typically the rotor can pivot on a pivot axis between a plurality of rotor positions, with each rotor position being spaced preferably 360/n° apart.

A prime/purge injection valve, in the "load" position permits loading of a sample into a sample loop at relatively atmospheric pressure while simultaneously allowing high pressure mobile phase to be pumped through a column.

In the "inject" position, the sample that was contained within the sample loop is injected into the high pressure stream and flushed through the column. Simultaneously, the sample port and associated switching channel can be flushed of any residual fluid, thus eliminating the possible contamination of future samples during the next loading cycle. This is a desirable feature that is not capable with other valve designs that have prime/purge inject capabilities.

In the "prime/purge" position, priming or purging of the high pressure pump and associated fluid lines is permitted by venting the pump outlet to a waste container that is essentially at atmospheric pressure. This feature exists with several other injection valves designs, but these other designs do not permit flushing of the sample port during the sample injection cycle.

The preferred multi-route selection valve for which n=5, permits the selection of flow between five different flow paths. Two of these flow paths permit flow between two independent columns, two additional flow paths permit the back flushing of one column onto another column, and the fifth flow path permits the bypass of both columns for rapid mobile phase change-out. The multi-route selection valve has a stator and rotor that are similar to the above mentioned prime/purge injection valve.

DESCRIPTION OF THE PREFERRED EMBODIMENTS

Figure 2:
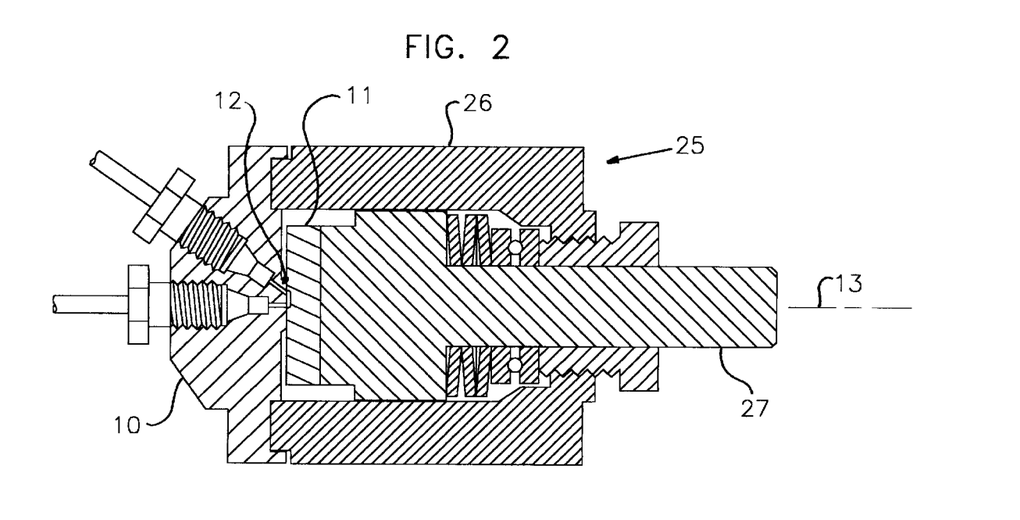
FIG. 2 is a sectional side view of a prime/purge injector or multi-route selector valve of the present invention.

FIG. 2 illustrates the preferred embodiment of a prime/purge injection valve 25. In one position, the valve can receive a sample to be analyzed from a syringe or other loading device, while simultaneously allowing a pump to deliver solvent at high pressure directly to a column. When the rotor is switched to another position, the sample contained within a sample loop is delivered to the chromatographic column or other analytical device. While the sample is being injected, a separate flow path exists that permits flushing of the sample port. This ensures the next sample to be loaded will not be contaminated from the prior sample. Switching the valve to a third rotor position, allows the pump outlet to be routed directly to waste, providing a means of priming or purging the pump and associated fluid lines.

FIG. 2 can also illustrate a preferred embodiment of the multi-route selection valve 25, which can receive the sample to be analyzed along with the solvent (from the column outlet port of the above described prime/purge injector or any current model injector) and divert the fluids through a selected one of n different flow paths. Both prime/purge injection valve and multi-route selection valves are comprised of a stator 10 mounted to a housing 26. Inside the housing is contained a rotor seal disc 11 mounted to a rotor shaft 27, that can pivot about an axis 13.

Valve assemblies according to the present invention preferably meet the following criteria. They should have a common stator port and n peripheral stator ports where n is the maximum number of peripheral ports equaling an odd integer greater than or equal to 5. Preferably n=5,7, or 9. More preferably n=5 or 9. It will be appreciated that the common port is a port capable of fluid communication with each of the peripheral stator ports, depending upon the orientation of the rotor. The spacing of the n peripheral ports preferably measures $360/n°$.

The rotor contains a distribution channel capable of fluid communication with the common port and at least one of the n peripheral ports. The rotor also contains $(n+1)/2-1$ switching channels capable of fluid communication between pairs of adjacent peripheral stator ports.

The flow systems connected to the valve are preferably comprised of terminal components and flow through components. Terminal components are any apparatus or device connected to the valve assembly by a single stator port. Flow through components are any apparatus or device connected to the valve assembly by more than one stator port. Typical examples of terminal and flow through components include: fluid pumps, needles, canulas, detectors, tubing, columns, solid phase support resins, filters, sample loops, waste drains, and injection or selection valves.

Figure 10:
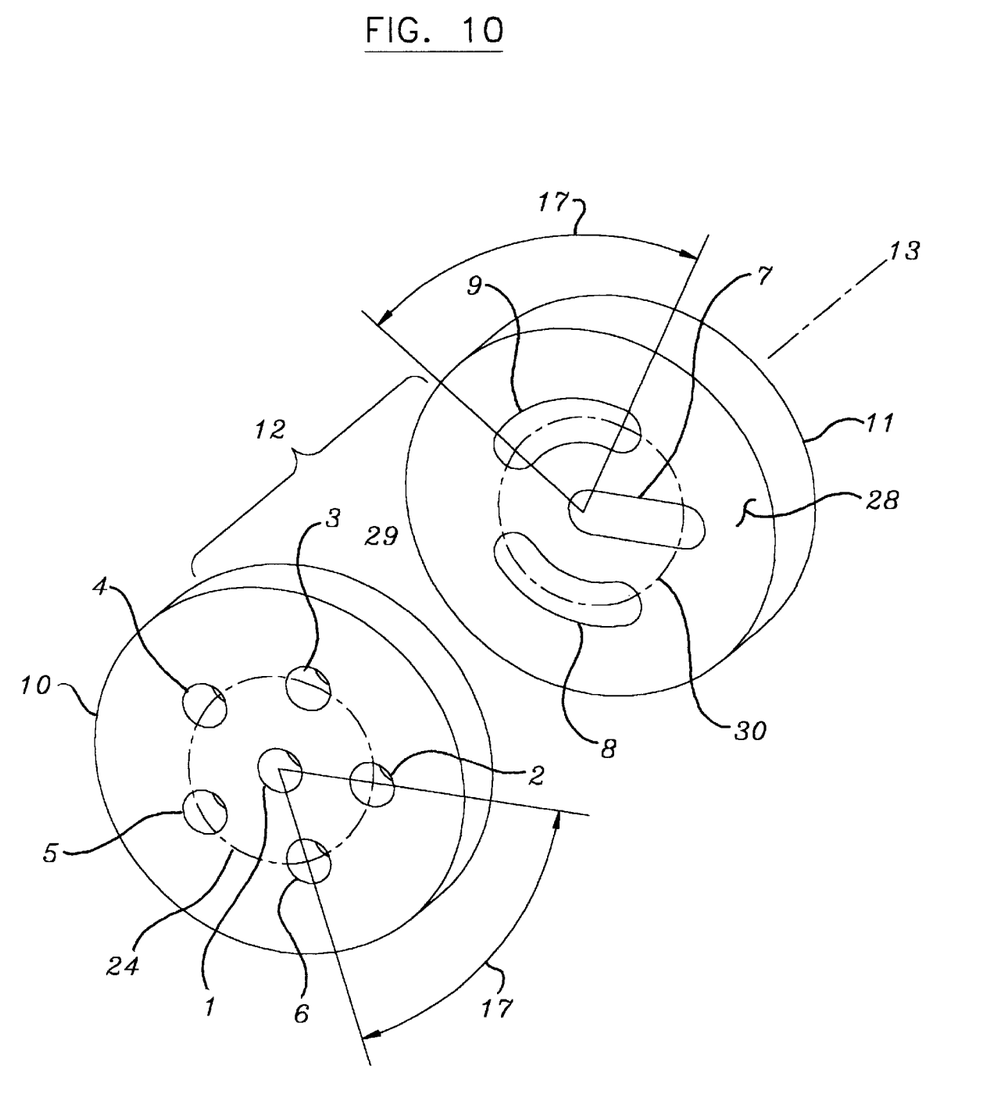
FIG. 10 is a simplified isometric view of the stator and rotor elements for either a prime/purge injection valve or a multi-route selection valve.

FIG. 10 illustrates a simplified isometric view of the present invention. The stator 10 is comprised of a common port 1 and n peripheral ports 2,3,4,5,6 where n is the maximum number of peripheral ports equaling an odd integer greater than or equal to five and for this example n=5. For convenience, the common port 1 is located along the axis 13. The remaining five ports 2–6 lie equally spaced apart by an angle 17 of $360/n°$ or $72°$ on an imaginary port circle 24 which is centered on the axis 13.

The rotor 11 has a lateral surface 28 which is comprised of a distribution channel 7 and $(n+1)/2-1$ switching channels 8 and 9. This lateral surface in close physical contact with the stator rear face 29 producing a pressure tight seal. Channel 7 provides a means to connect the common port 1 to any of the n peripheral ports 2–6 that lie on the imaginary port circle 24. The switching channels 8 and 9 each span circumferentially through an arc circle of angle 17 of $360/n°$ or $72°$, with the arc circle having a diameter 30 of equal diameter to the imaginary port circle 24. Channels 8 and 9 communicate flow between a plurality of adjacent peripheral stator ports as the rotor turns (as best seen by a series of views taken along the axis 13, see FIGS. 7A through 7E).

Figure 14:
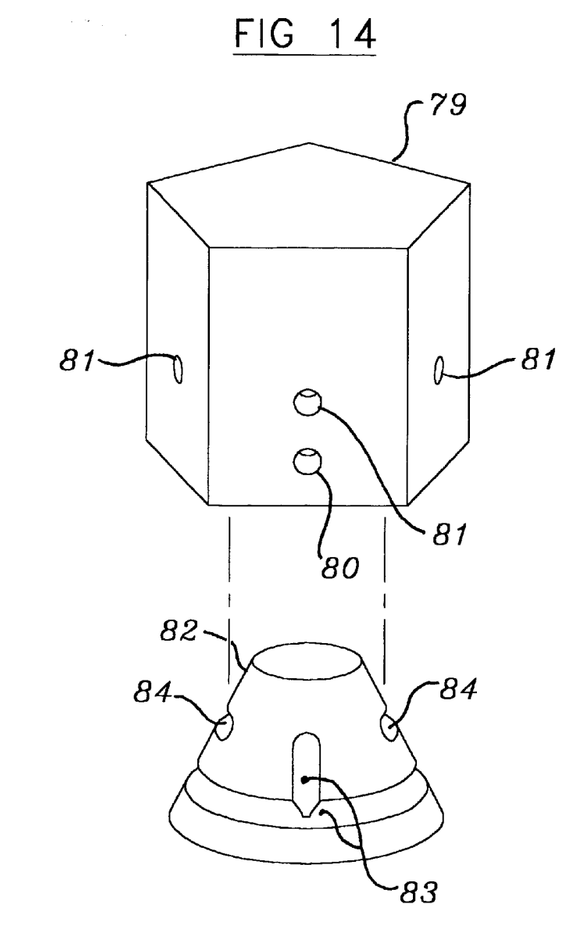
FIG. 14 shows a view for a conical rotor design of the present invention.
Figure 15:
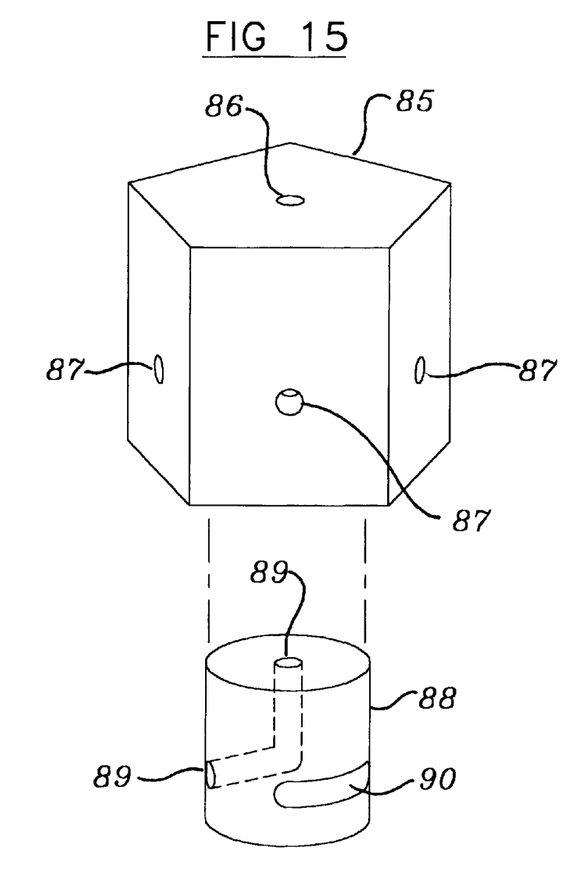
FIG. 15 shows a view for a cylindrical rotor design of the present invention.

FIGS. 14 and 15 show two examples of a less preferred design of the present invention. The valve assemblies comprise a housing (79 or 85) which are comprised of a common port (80 or 86) and n peripheral ports (81 or 87) where n is the maximum number of peripheral ports equaling an odd integer greater than or equal to five. Contained within the housing and in close physical contact therewith is a rotor (82 or 88) which are respectively conical and cylindrical in shape. The rotors are comprised of a distribution channel (83 or 89) and $(n+1)/2-1$ switching channels (84 or 90).

Although other valve designs contain conical and cylindrical rotor seals, these other designs do not permit prime/purge injection with the capability of flushing the sample port in the inject position, or Multi-Route Selection Valve with sample enrichment capabilities using a single pump.

1. PRIME/PURGE INJECTION VALVE: N=5

Figures 3A, 3B, 3C:
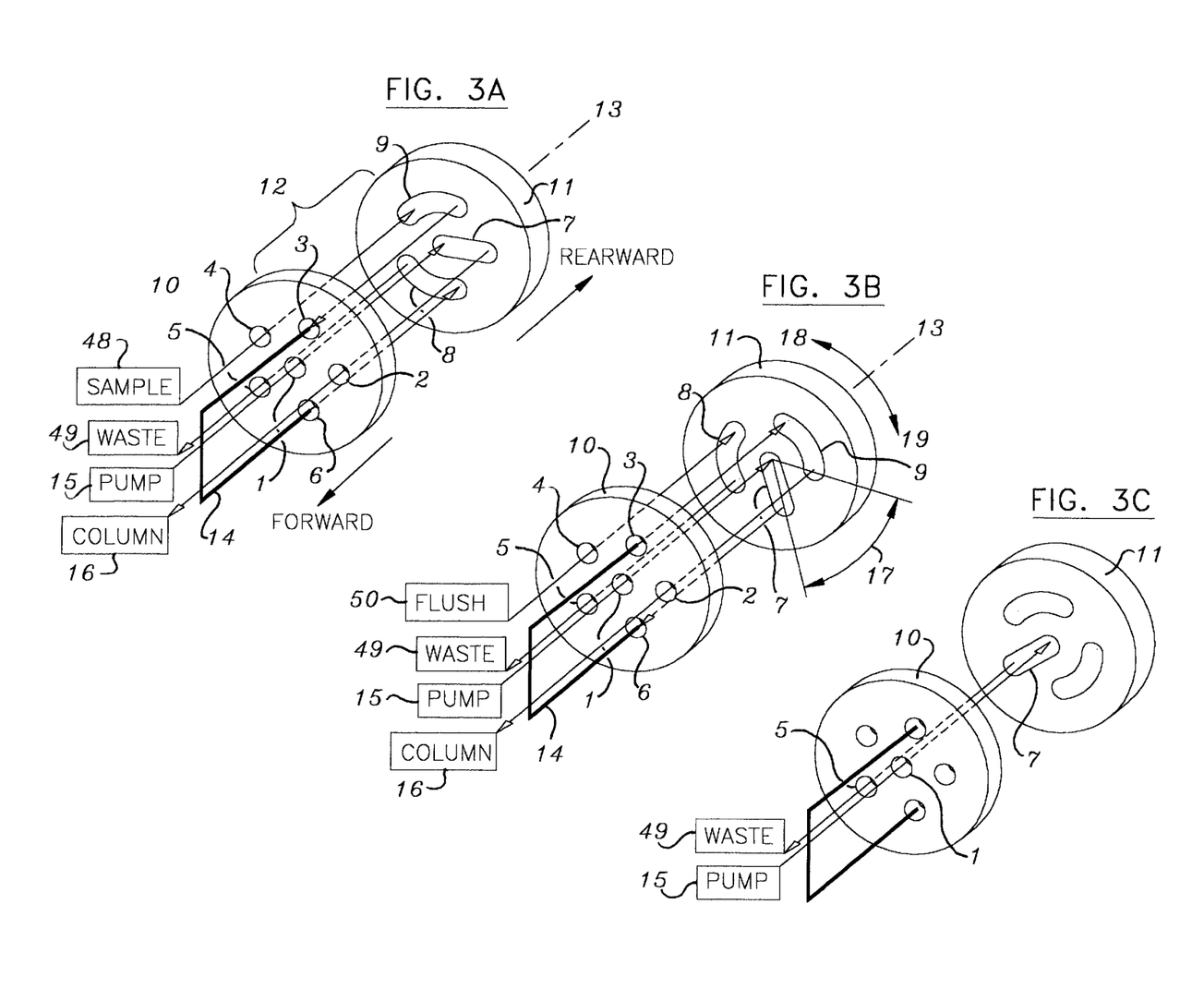
FIG. 3A is a simplified exploded isometric view of a prime/purge injection valve shown in the load position.
FIG. 3B is a simplified exploded isometric view of a prime/purge injection valve shown in the inject position.
FIG. 3C is a simplified exploded isometric view of a prime/purge injection valve shown in the prime/purge position.

FIGS. 3A through 3C show the simplified isometric view of the preferred stator 10 where n=5 and the rotor 11 for the three different rotor positions "load", "inject", and "prime/purge" respectively. The stator is comprised of six passages or ports labeled 1,2,3,4,5, and 6 which extend axially through the stator. Common stator port 1 is located along the rotors axis 13, while peripheral stator ports 2–6 lie on an imaginary port circle. A sample loop 14 is connected between stator ports 3 and 6. At the interface 12 each end of the distribution channel 7 and switching channels 8 and 9, align with the six passages to provide an uninterrupted fluid path from one stator port to another stator port.

FIG. 3A, shows the injection valve with the rotor in the "load" position, wherein it is used to pass the mobile phase (solvent) through a column 16 (typically at pressures between 500 to 7000 psi) while simultaneously permitting the loading of a sample (essentially at atmospheric pressure) into a sample loop 14. A pump 15 pumps a solvent into the common port 1 where the solvent passes rearwardly through the stator to the interface 12 and into the distribution channel 7. The fluid then travels radially with respect to axis 13 along the distribution channel 7 to the stator port 2. The fluid moves forwardly through port 2 to the front end of port 2 which is connected to column 16. To analyze a sample originally contained in a syringe or other metering device, the sample 48 is injected into sample port 4 (basically at atmospheric pressure). The fluid sample flows rearwardly through port 4 to the interface 12 and into the switching channel 9. Next the fluid sample travels circumferentially along switching channel 9 to port 3. The fluid sample then travels forwardly through port 3 and into a sample loop 14 which is of known volume and spans between sample loop ports 3 and 6. Any solvent that previously occupied the sample loop is flushed out traveling rearwardly through port 6 to the interface 12 and into the switching channel 8. The flushed out solvent then travels circumferentially along switching channel 8 to port 5. Finally the solvent travels forwardly through port 5 and out to a waste container 49.

After a sample has been loaded into the sample loop 14, the sample can then be injected into the column. This is accomplished by rotating the rotor in the direction 19 by an angle 17 of 72° from the LOAD position to the INJECT position as shown in FIG. 3B. In this position, solvent under high pressure from the pump enters the valve through the pump port 1 and travels rearwardly through the stator to the interface 12, then radially along distribution channel 7 to port 6. Solvent then flows forwardly through port 6 which is connected to one end of the sample loop 14. The sample that previously occupied the sample loop is flushed out under high pressure traveling rearwardly through port 3, to the interface 12 then circumferentially along switching channel 9 to port 2. The sample is then pumped forwardly through port 2 and out to a column 16 where the sample can be analyzed.

A feature not capable with other "prime/purge injection" valves is the flushing of the sample port and associated switching channels while the valve is in the "inject" position. This is accomplished as follows. A syringe is loaded with solvent or other flushing fluid 50 which can be pumped (essentially at atmospheric pressure) into the sample port 4, where it travels rearwardly through the stator to the interface 12 and into switching channel 8. The flushing fluid then travels circumferentially along switching channel 8 to port 5. It then travels forwardly through port 5 and out to a waste container 49. This feature is important because it permits flushing of the sample port 4 and switching channel 8 of any residual sample from the previous loading cycle which could contaminate the next sample to be loaded.

From the INJECT position, the rotor can be rotated back an angle 17 of 72° in the direction 18 to the LOAD position for loading of another sample to be analyzed, or the rotor can be rotated an additional 72° in the direction 19 to the PRIME/PURGE position. In the PRIME/PURGE position the outlet from the pump is vented to essentially atmospheric pressure via the waste line. This permits the priming of the high pressure pump by bleeding the pump and associated fluid lines of any air during startup of the chromatographic system. Another function that can be accomplished in the PRIME/PURGE position is the purging of the pump of any unwanted solvent during solvent change over.

FIG. 3C shows an isometric view of the stator 10 and rotor 11 for the preferred embodiment in the PRIME/PURGE position. Flow from the pump 15 enters the stator port 1 and travels rearwardly through the stator to the interface 12, and into the distribution channel 7. The fluid then flows radially along distribution channel 7 to port 5 and then forwardly through port 5 and out to either a waste container 49 or a suctioning syringe.

Figure 4A:
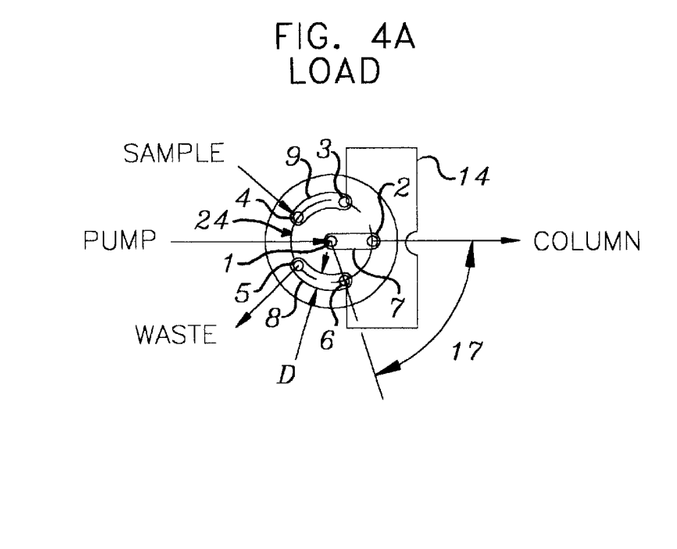
FIG. 4A is simplified flow diagram of a prime/purge injection valve looking along the pivot axis and shown in the load position, as shown in FIG. 3A.
Figure 4B:
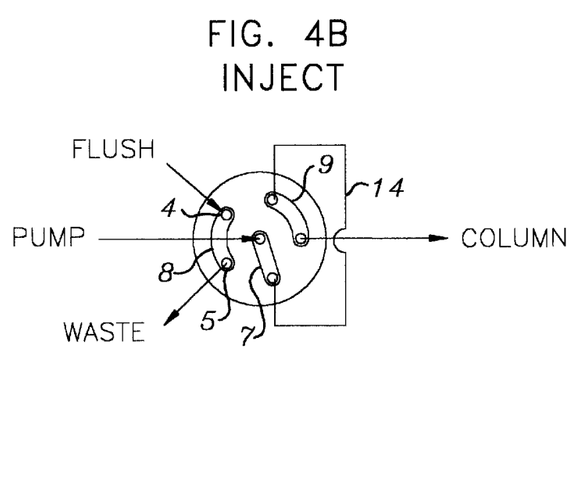
FIG. 4B is simplified flow diagram of a prime/purge injection valve looking along the pivot axis and shown in the inject position, as shown in FIG. 3B.
Figure 4C:
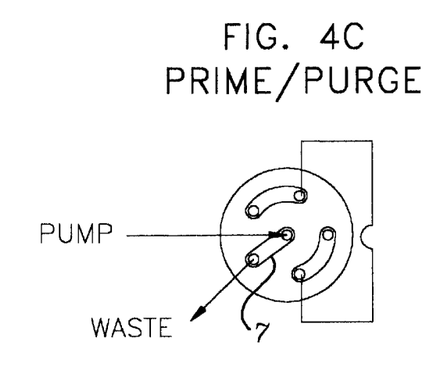
FIG. 4C is simplified flow diagram of a prime/purge injection valve looking along the pivot axis and shown in the prime/purge position, as shown in FIG. 3C.

FIGS. 4A–4C are simplified axial views of FIGS. 3A–3C respectively. It can be seen that stator port 1 is located along the rotors axis of rotation and ports 2, 3, 4, 5, and 6 are equally space by an angle 17 of 72° on an imaginary port circle 24. Distribution channel 7 is a radial groove that extends from the common stator port 1 to any of the peripheral stator ports 2–6. It can also be seen that switching channels 8 and 9 each span an arc of angle 17 of 72° thus allowing uninterrupted flow between adjacent stator ports. It may be noted that the interconnect channels have a specified width D, and it is assumed that each end of the channels is largely like a half circle of that diameter D. In FIGS. 4A–4C, the distribution channels 7 and switching channels 8, and 9 are drawn slightly larger than the stator ports 1–6 to aid in distinguishing them; they are preferably of the same widths.

FIG. 4A shows the rotor in the "load" position wherein the switching channels 8 and 9 are positioned to permit filling of a sample loop 14. Meanwhile, distribution channel 7 is positioned to pass solvent from a high pressure pump to a column. FIG. 4B shows the rotor in the "inject" position wherein the distribution channel 7 and switching channel 9 connect the high pressure pump to a column via the sample loop 14, thus flushing the sample contained within the sample loop onto the column. Meanwhile, switching channel 8 permits flushing of ports 4 and 5 of any residual sample. FIG. 4C shows the rotor in the "prime/purge" position wherein distribution channel 7 connects the high pressure pump discharge to ambient pressure via the waste outlet.

2. PRIME/PURGE INJECTION VALVE: N=7

Figure 11A:
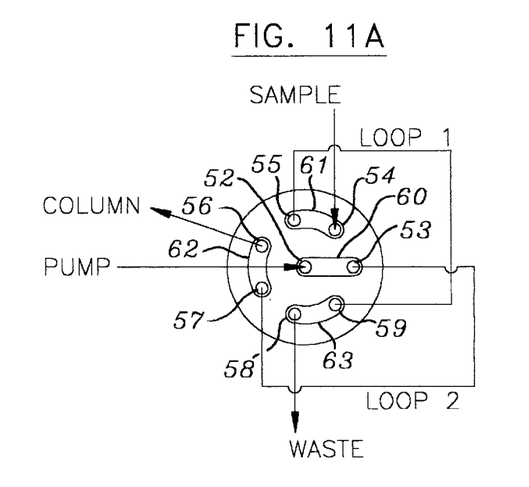
FIGS. 11A–11C are axial views showing possible rotor positions for a dual sample loop injection valve where N=7.
Figure 11B:
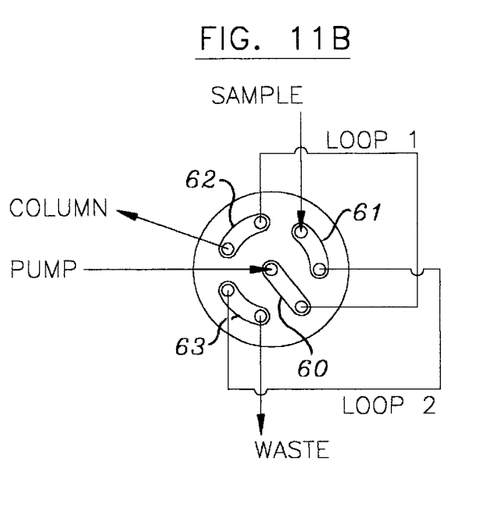
Figure 11C:
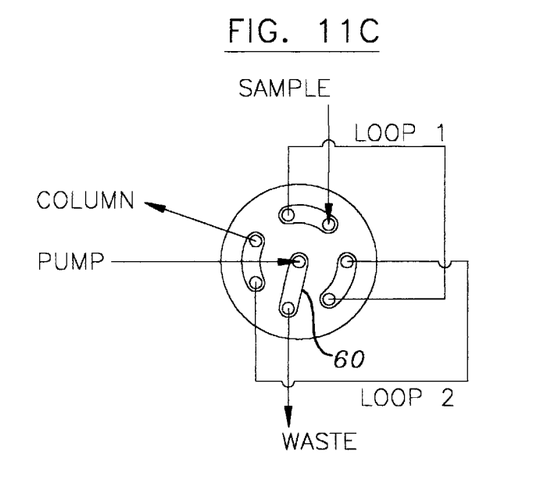

FIGS. 11A–C show a dual-sample loop injection valve for three separate positions. In these figures, the stator has a common port 52 and n=7 peripheral ports 53–59. The common port is connected to a terminal component labeled PUMP while three of the peripheral ports are connected to three additional terminal components labeled SAMPLE, WASTE, and COLUMN. The remaining four port connections are attached to two separate flow through components labeled LOOP 1 and LOOP 2 which may be of equal or different volumes. The rotor consists of a distribution channel 60 and three switching channels 61,62,63. The spacing of the peripheral stator ports and rotor channels measures preferably 51.4°.

FIG. 11A shows the valve in the "LOAD1/INJECT2" wherein the rotor is positioned such that distribution channel 60 and switching channel 62 permit flow from the pump to the column via LOOP 2. Simultaneously, a sample can be loaded into LOOP 1 via port 54 and switching channel 61 and any solvent that previously occupied LOOP 1 is directed to waste via switching channel 63.

FIG. 11 B shows the valve in the "INJECT1/LOAD2" position wherein the rotor is rotated in the clockwise direction by preferably 51.4° from that shown in FIG. 11A. The rotor's distribution channel 60 and switching channel 62 allow the pump to flush the sample contained in LOOP 1 onto the column. Simultaneously, a sample can be loaded into LOOP 2 via switching channel 61 and any solvent that previously occupied LOOP 2 is directed to waste via switching channel 63.

FIG. 11C shows the valve in the "PRIME/PURGE" position wherein the rotor is rotated in the clockwise direction by an additional 51.4° from that shown in FIG. 11B. In this position the pump is vented to essentially atmospheric pressure through the waste port via the distribution channel 60. This position would facilitate priming or purging of the pump.

3. PRIME/PURGE INJECTION VALVE: N=9

Figure 12A:
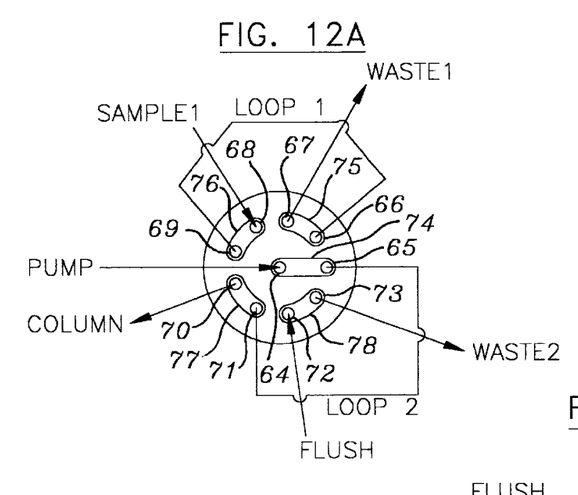
FIGS. 12A–12C are axial views showing possible rotor positions for a dual sample injection valve where N=9.
Figure 12B:
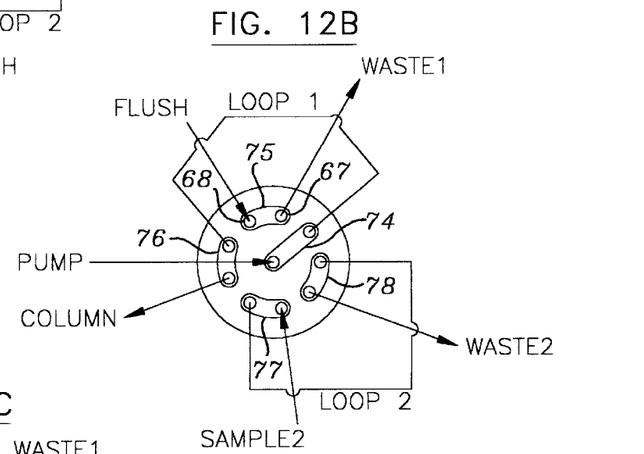
Figure 12C:
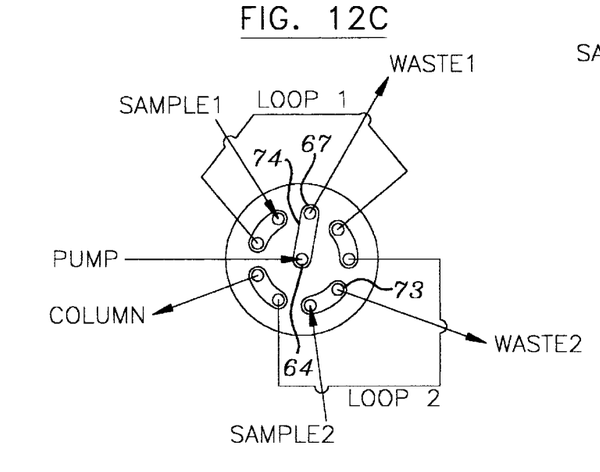

FIGS. 12A–12C show a "dual sample injection" valve for three separate positions. In these figures, the stator has a common port 64 and n=9 peripheral ports 65–73. The common port is connected to a terminal component labeled PUMP while five of the peripheral ports are connected to five additional terminal components labeled SAMPLE1, WASTE1, SAMPLE2, WASTE2, and COLUMN (note that SAMPLE1 and SAMPLE2 may be interchanged with a flushing solution to permit flushing of the sample ports prior to loading the next sample). The remaining four port connections are attached to two separate flow through components labeled LOOP 1 and LOOP 2 which may be of different volumes. The spacing between the peripheral stator ports measures preferably 40°. The rotor consists of a distribution channel 74 and four switching channels 75–78.

FIG. 12A shows the valve in the "LOAD1/INJECT2" position wherein the rotor is positioned such that distribution channel 74 and switching channel 77 permit flow from the pump to the column via LOOP 2. Simultaneously, a sample can be loaded into LOOP 1 via switching channel 76 and any solvent that previously occupied LOOP 1 is directed to WASTE 1 via switching channel 75. To reduce the possibility of contaminating of the next sample to be loaded into LOOP 2, a flushing solvent can be used to flush switching channel 78 and ports 72 and 73 of any residual sample.

FIG. 12B shows the valve in the "INJECT1/LOAD2" position wherein the rotor is rotated in the counterclockwise direction by preferably 40° from that shown in FIG. 12A. The rotor's distribution channel 74 and switching channel 76 permit the pump to flush the sample contained in LOOP 1 onto the column. Simultaneously, a sample can be loaded into LOOP 2 via switching channel 77 and any solvent that previously occupied LOOP 2 is directed to waste via switching channel 78. To reduce the possibility of contaminating the next sample to be loaded into LOOP 1, a flushing solvent can be used to flush switching channel 75 and ports 68 and 67 of any residual sample.

FIG. 12C shows the valve in the "PRIME/PURGE" position wherein the rotor is rotated in the counterclockwise direction by an additional 40°. In this position the pump is vented to essentially atmospheric pressure through the waste port 67 via the distribution channel 74. This position would facilitate priming or purging of the pump. An alternate prime/purge position would occur if the rotor is positioned such that the distribution channel 74 is aligned such that it connects the common port 64 with the peripheral port 73.

4. MULTI-ROUTE SELECTION VALVE: N=5

Multi-Route selection valves for the present invention preferably have stator port connections to two terminal components, and n–1 stator port connections to (n+1)/2–1 flow through components. The flow through components are preferably connected to adjacent peripheral stator ports. Exactly one flow path will directly connect the two terminal components with no intervening flow through components. FIGS. 6A through 6E show the simplified isometric view of the stator 10 wherein n=5, and rotor 11 for the five different rotor positions. The stator and rotor are of the same design as the preferred prime purge injection valve.

Figures 6A, 6B, 6C:
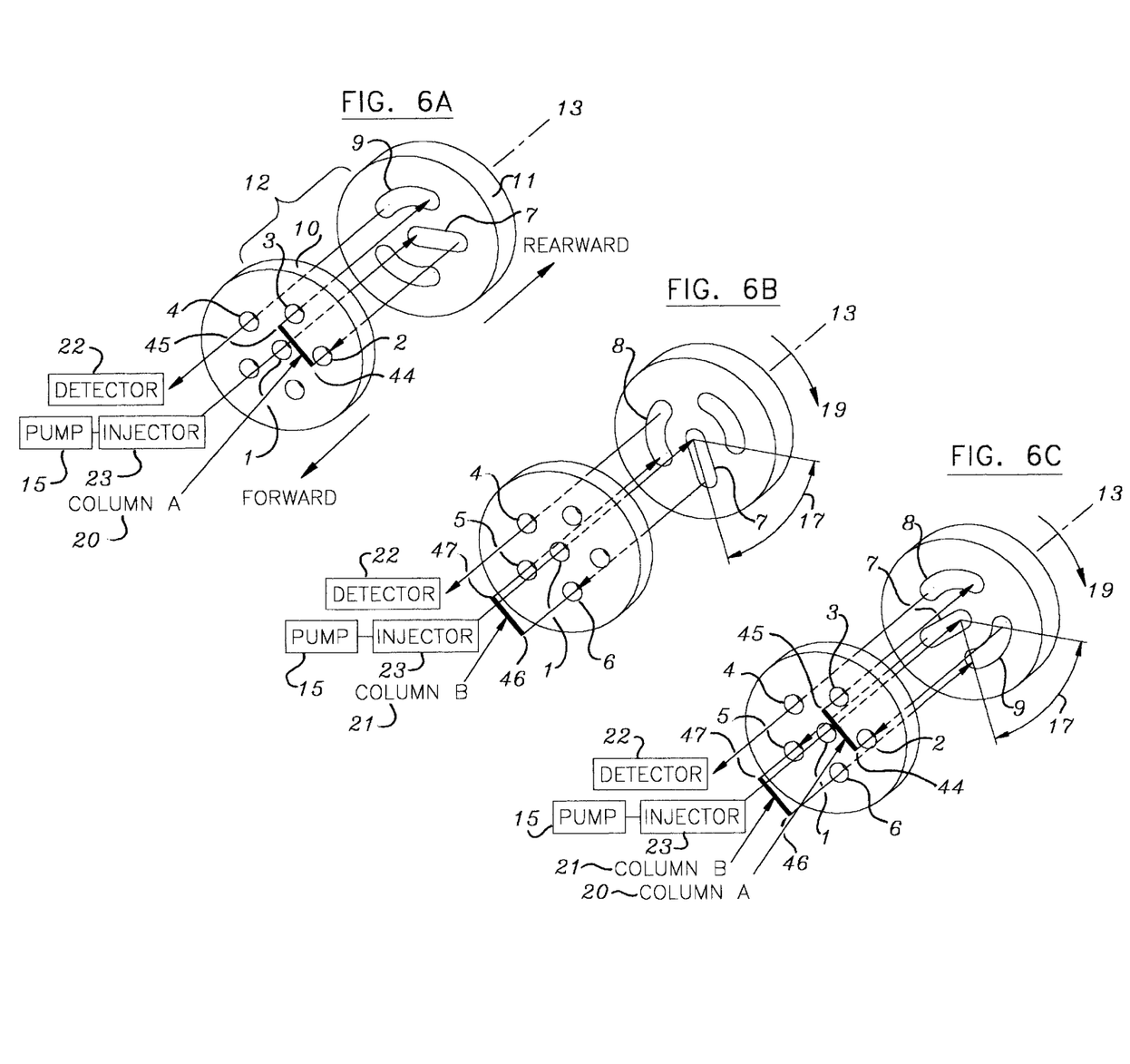
FIG. 6A is a simplified exploded isometric view of a multi-route selection valve shown with column A selected.
FIG. 6B is a simplified exploded isometric view of a multi-route selection valve shown with column B selected.
FIG. 6C is a simplified exploded isometric view of a multi-route selection valve shown with column B being back flushed onto column A.

FIG. 6A shows the rotor in a first position, wherein it is used to pass mobile phase (solvent) and sample through column 20 which is identified as "column A". A pump 15 pumps a solvent through an injector 23 and into the common stator port 1 at high pressure (typically between 500 to 7000 psi). The fluid passes rearwardly through the stator to the interface 12 and into distribution channel 7. The fluid then travels radially with respect to axis 13 to port 2. The fluid then moves forwardly through port 2 where it enters the head 44 of column A 20. The fluid flows through the column and exits out the tail 45 of column A which is connected to the front of port 3. The fluid flows through port 3 to the interface 12 and then circumferentially along switching channel 9 to port 4. The fluid flows forwardly through port 4, where it exits the valve and flows to a detector 22 to be analyzed.

FIG. 6B shows the selection valve after the rotor has been rotated in the direction 19 by an angle 17 of 72° from the initial position of FIG. 6A. In this new position, fluid is pumped through column 21 which is identified as "column B". The pump 15 pumps a solvent through the injector 23 and into the common stator port 1. The fluid passes rearwardly through the stator to the interface 12 and into the distribution channel 7. The fluid travels radially with respect to axis 13 along distribution channel 7 to port 6. The fluid moves forwardly through port 6 where it enters the head 46 of column B 21. The fluid flows through the column and exits out the tail 47 of column B which is connected to the front of port 5. The fluid flows rearwardly through port 5 to the interface 12 and then circumferentially along switching channel 8 to port 4. The fluid flows forwardly through port 4, where it exits the valve and flows to a detector 22 to be analyzed.

FIG. 6C shows the selection valve after the rotor 11 has been rotated in the direction 19 by an angle 17 of 72° from the position of FIG. 6B. In some applications, large volumes of sample may be injected into a pre-column (column B) where the trace components are concentrated (see FIG. 6B for flow path). After valve switch (FIG. 6C) the trace components from the sample are back flushed off the head 46 of the pre-column (column B) 21 and onto the analytical column (column A) 20 where the concentrated trace components can be further analyzed. In the configuration of FIG. 6C, a pump 15 pumps solvent through the injector 23 and into the common stator port 1. The fluid passes rearwardly through the stator to the interface 12 and into the distribution channel 7. The fluid then travels radially with respect to the axis 13 along distribution channel 7 to port 5. The fluid moves forwardly through port 5 to the tail 47 of column B 21. The fluid back flushes through column B carrying the trace components that were previously concentrated on the head 46 of column B. Next the fluid flows rearwardly through port 6 to the interface 12 and then circumferentially along switching channel 9 to port 2. The fluid then moves forwardly through the port 2 to the head 44 of column A 20. The fluid flows through column A and exits out the tail 45 where it flows rearwardly through port 3 to the interface 12 and then circumferentially along switching channel 8 to port 4. The fluid flows forwardly through port 4 where it exits the front of the valve and flows into a detector 22 to be analyzed.

Figures 6D, 6E:
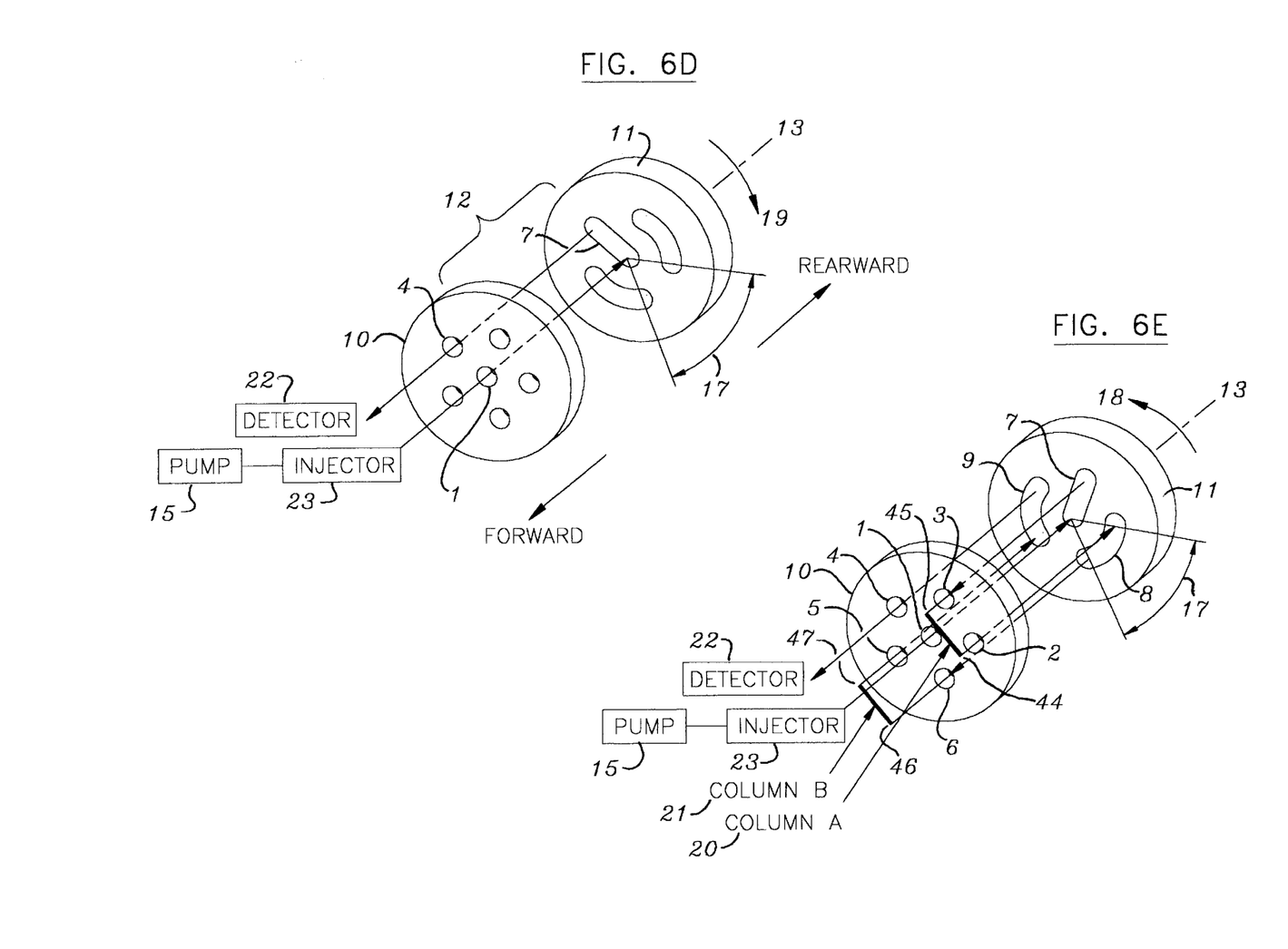
FIG. 6D is a simplified exploded isometric view of a multi-route selection valve shown in the bypass position.
FIG. 6E is a simplified exploded isometric view of a multi-route selection valve shown with column A being back flushed onto column B.

FIG. 6D shows the selection valve after the rotor 11 has been rotated in the direction 19 by an angle 17 of 72° from the position of FIG. 6C. The configuration of FIG. 6D allows flushing the flow paths in the analytical system including the pump, injector and detector without passing fluid through either column A or column B. In FIG. 6D changeover to a new solvent can be accomplished at fluid velocities not possible when the fluid must pass through the highly restrictive and pressure sensitive columns. The pump 15 pumps a solvent or flush solution through the injector 23 and into the common stator port 1. The fluid passes rearwardly through port 1 to the interface 12 and into distribution channel 7. The fluid then travels radially with respect to the axis 13 along distribution channel 7 to port 4. The fluid moves forwardly through port 4, where it exits the valve and flows through a detector 22 and out to a waste container not shown.

FIG. 6E shows the selection valve after the rotor has been rotated in the direction 18 by an angle 17 of 72° from the initial position of FIG. 6A. In the event that column A 20 is a pre-column and column B 21 is an analytical column then we can perform a similar operation described for FIG. 6C. In the configuration of FIG. 6E, a pump 15 pumps solvent through an injector 23 and into the common stator port 1. The fluid passes rearwardly through the stator to the interface 12 and into the distribution channel 7. The fluid then travels radially with respect to the axis 13 along distribution channel 7 to port 3. The fluid moves forwardly through port 3 to the tail 45 of column A 20. The fluid back flushes through column 20 carrying the trace components that were previously concentrated on the head 44 of the column A. Next, the fluid flows rearwardly into port 2 to the interface 12 and then circumferentially along switching channel 8 to port 6. The fluid then moves forwardly through the port 6 to the head 46 of column B 21. The fluid flows through column B and exits out the tail 47 where it enters port 5. The fluid flows rearwardly through port 5 to the interface 12 and then circumferentially along switching channel 9 to port 4. The fluid flows forwardly through port 4 where it exits the front of the valve and flows to a detector 22 to be analyzed.

FIGS. 7A–7E are simplified axial views of FIGS. 6A–6E, respectively. It can be seen that common stator port 1 is located along the rotors axis of rotation and ports 2, 3, 4, 5, and 6 are equally space by an angle 17 of 72° on an imaginary port circle 24. Distribution channel 7 is a radial groove that extends from the axis of rotation out to port 2 which lies on the imaginary port circle 24. It can also be seen that switching channels 8 and 9 each span an arc of angle 17 of 72° thus allowing uninterrupted flow between adjacent stator ports.

Figure 7A:
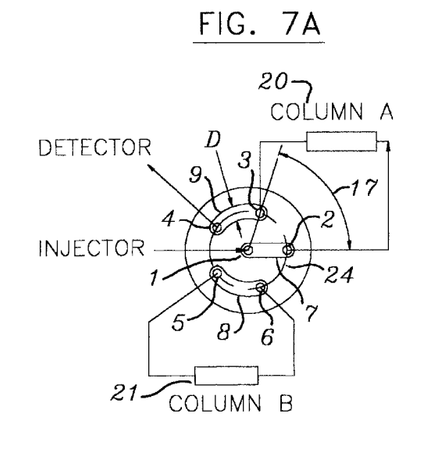
FIG. 7A is simplified flow diagram of a multi-route selection valve looking along the pivot axis and shown with column A selected, as shown in FIG. 6A.
Figure 7B:
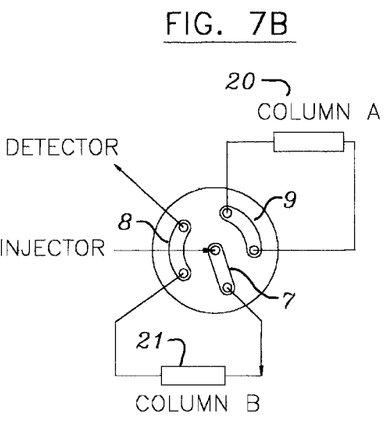
FIG. 7B is simplified flow diagram of a multi-route selection valve looking along the pivot axis and shown with column B selected, as shown in FIG. 6B.
Figure 7C:
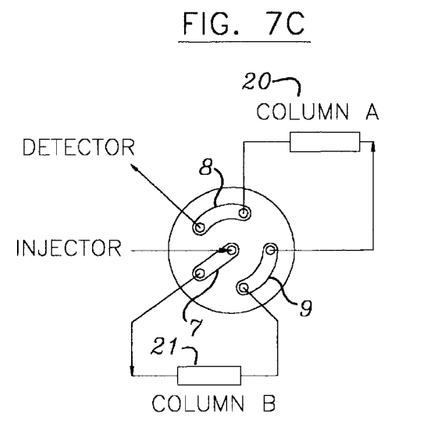
FIG. 7C is simplified flow diagram of a multi-route selection valve looking along the pivot axis and shown with column B being back flushed onto column A, as shown in FIG. 6C.
Figure 7D:
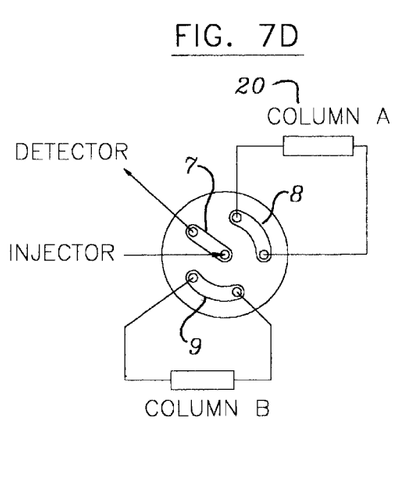
FIG. 7D is simplified flow diagram of a multi-route selection valve looking along the pivot axis and shown in the bypass position, as shown in FIG. 6D.
Figure 7E:
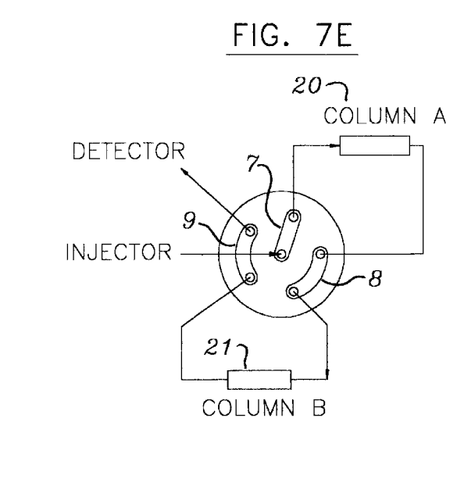
FIG. 7E is simplified flow diagram of a multi-route selection valve looking along the pivot axis and shown with column A being back flushed onto column B, as shown in FIG. 6E.

FIG. 7A shows the rotor in a position wherein the distribution channel 7 and switching channel 9 are positioned to pass fluid through column A 20 and out to a detector. Meanwhile, column B 21 is connected head to tail by switching channel 8. FIG. 7B shows the rotor in a position wherein the distribution channel 7 and switching channel 8 are positioned to pass fluid through column B 21 and out to a detector. Meanwhile, column A 20 is connected head to tail by switching channel 9. FIG. 7C shows the rotor in a position wherein the distribution channel 7, and switching channels 8 and 9 are positioned to backflush fluid through column B 21, this back flush is then passed through column A 20 and out to a detector. FIG. 7D shows the rotor in a position wherein the distribution channel 7 bypasses both columns and passes fluid directly to the detector. Meanwhile switching channel 8 connects column A head to tail, and switching channel 9 connects column B head to tail. FIG. 7E shows the rotor in a position wherein the distribution channel 7, and switching channels 8 and 9 are positioned to back flush fluid through column A 20, this back flush is then passed through column B 21 and out to a detector.

Multi-Route selection valves for which n=7 and n=9 would have the same rotor and stator design as the previously described prime/purge injection valves wherein the stator is comprised of a common port and n peripheral ports. The rotor is comprised of a distribution channel and $(n+1)/2-1$ switching channels. Stator port connections to a multi-route selection valve would preferably contain 2 terminal connections and n−1 port connections to $(n+1)/2-1$ flow through components.

Although particular embodiments of the invention have been described and illustrated herein, it is recognized that modifications and variations including differing plumbing configurations for flow through and terminal component may readily occur to those skilled in the art, and consequently, it is intended that the claims be interpreted to cover such modifications and equivalents.

I claim:

1. A valve assembly for the regulation of fluid flow, comprising:

a stator comprising a common port and n peripheral ports, wherein n is the maximum number of peripheral ports equaling an odd integer greater than or equal to 5; and a rotor positioned to rotate against the stator comprising:
     a distribution channel capable of fluid communication with the common port and each of the peripheral ports upon rotation of the rotor; and
     $(n+1)/2-1$ switching channels, each switching channel capable of simultaneous fluid communication with at least two of the peripheral ports upon rotation of the rotor.

2. The valve assembly of claim 1 wherein the spacing between the n peripheral stator ports measures $360/n°$.

3. The valve assembly of claim 1 wherein the length of each switching channel spans an arc of $360/n°$.

4. The valve assembly of claim 1 wherein n equals 5.

5. The valve assembly of claim 1 wherein n equals 9.

6. The valve assembly of claim 1 wherein the rotor has a lateral face comprised of a distribution channel and $(n+1)/2-1$ switching channels.

7. The valve assembly of claim 1 wherein the rotor is cylindrical.

8. The valve assembly of claim 1 wherein the rotor is conical.

9. The valve assembly of claim 1 used for the purpose of priming or purging a pump, for receiving a sample to be analyzed from a loading source, and for injecting said sample into an analyzing instrument.

10. The valve assembly of claim 9 wherein stator ports are connected to terminal components selected from the group consisting of fluid pumps, sample needles, tubing, columns, solid phase support resins, waste drains, sample loops, and detectors.

11. The valve assembly of claim 9 wherein stator ports are connected to flow-through components selected from the group consisting of tubing, in columns, solid phase resins, and sample loops.

12. The valve assembly of claim 1 used for the purpose of selecting multiple flow paths through an analyzing instrument.

13. The valve assembly of claim 12 wherein stator ports are connected to terminal components selected from the group consisting of fluid pumps, sample injector, tubing, columns, solid phase support resins, waste drains, sample loops and detectors.

14. The valve assembly of claim 12 wherein stator ports are connected to flow-through components selected from the group consisting of tubing, columns, sample loops, and solid phase support resins.

15. The valve assembly of claim 12 wherein there exist two stator port connections to two terminal components; and there exist (n−1) stator port connections to $(n+1)/2-1$ flow through components.

* * * * *